(12) United States Patent
Baag (10) Patent No.: US 8,755,904 B2
(45) Date of Patent: Jun. 17, 2014

(54) CIRCUIT ARRANGEMENTS FOR GENERATING CURRENTS AND THE APPLICATION THEREOF

(71) Applicant: inomed Medizintechnik GmbH, Emmendingen (DE)

(72) Inventor: Matthias Baag, Blankenfelde (DE)

(73) Assignee: inomed Medizintechnik GmbH, Emmendingen (DE)

( * ) Notice: Subject to any disclaimer, the term of this patent is extended or adjusted under 35 U.S.C. 154(b) by 0 days.

(21) Appl. No.: 13/934,418

(22) Filed: Jul. 3, 2013

(65) Prior Publication Data
US 2014/0012121 A1 Jan. 9, 2014

(30) Foreign Application Priority Data
Jul. 3, 2012 (DE) .......................... 10 2012 013 190

(51) Int. Cl.
*A61N 1/00* (2006.01)
(52) U.S. Cl.
USPC ................. 607/115; 607/4; 607/5; 607/9

(58) Field of Classification Search
USPC .............................................. 607/4–5, 9, 115
See application file for complete search history.

(56) References Cited

U.S. PATENT DOCUMENTS

2010/0324618 A1 12/2010 Wanasek

*Primary Examiner* — Nicole F Lavert
(74) *Attorney, Agent, or Firm* — Volpe and Koenig, P.C.

(57) ABSTRACT

Electronic circuit arrangements for generating at least two different constant currents at a load resistor, including a bridge circuit (especially an H bridge=H bridge circuit) having at least (in the case of an H bridge, precisely) four legs, and switching elements and a bridge branch between the legs, in which the load resistor is inserted, and at least two current sources which are connected to the legs of the bridge circuit in such a manner that it provides for current via one of the legs through the bridge branch and through a leg, connected to the other end of the bridge branch, with a corresponding switch position, the at least two current sources being adjustable if desired. The use of the circuit arrangement for generating such stimulation currents and corresponding procedures currents and methods.

14 Claims, 8 Drawing Sheets

CIRCUIT ARRANGEMENTS FOR GENERATING CURRENTS AND THE APPLICATION THEREOF

INCORPORATION BY REFERENCE

The following documents are incorporated herein by reference as if fully set forth: German Patent Application No. 102012013190.9, filed Jul. 3, 2012.

BACKGROUND

The invention relates to an (especially polyphase, especially biphase) electronic circuit arrangement (especially suitable or especially configured for generating at least two different stimulation currents in medicine) for generating at least two different constant currents, especially of different (antiphase) polarity, at a load resistor, comprising a bridge circuit (especially an H bridge=H bridge circuit) having at least (in the case of an H bridge, precisely) four legs, and switching elements and a bridge branch between the legs, in which the load resistor can be inserted, and a current source which is connected to the legs of the bridge circuit in such a manner that it provides for a current via one of the legs through the bridge branch through a leg, connected to the other end of the bridge branch, in the case of a corresponding switch position, the use of the circuit arrangement for generating such stimulation currents and corresponding procedures and methods.

Figure 1:
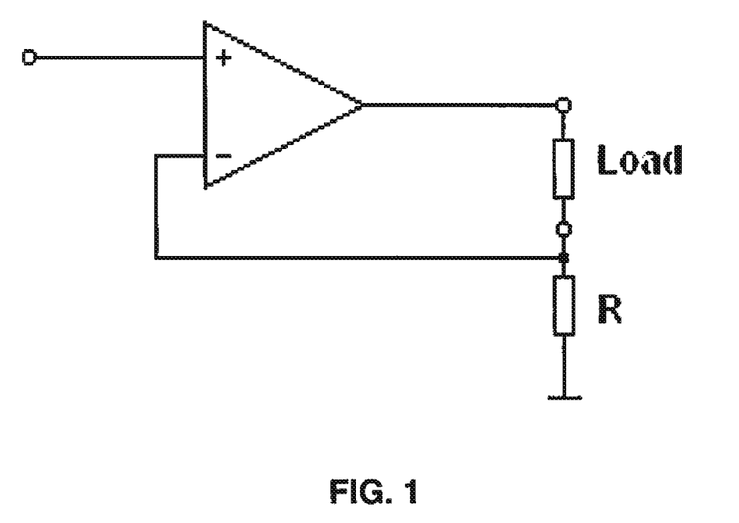
FIG. 1 shows diagrammatically a simplified example of a bipolar current source with OPA from the prior art.

For the purpose of generating constant currents, feedback-type operational amplifier circuits have usually been used as current source which, due to their operating principle, always needed a certain quiescent current for stabilizing their operating point. Due to the principle involved, this led to an increased power consumption, especially in the case of high open-circuit voltages, even at times at which the output current is zero. In addition, the use of operational amplifiers (OPA) greatly limited the possibility of a low open-circuit voltage since the OPA needs a minimum operating voltage due to the principle involved. FIG. 1 shows a simplified example of such a bipolar current source with OPA. "Load" is here the load resistor, for example tissue, organs or body parts (such as the head) of a patient which are to be stimulated by current flow in the case of a patient stimulation.

Unipolar current sources which have a FET (such as MOSFET) or transistor as a switching element in the output branch no longer have such a disadvantage.

Figure 2:
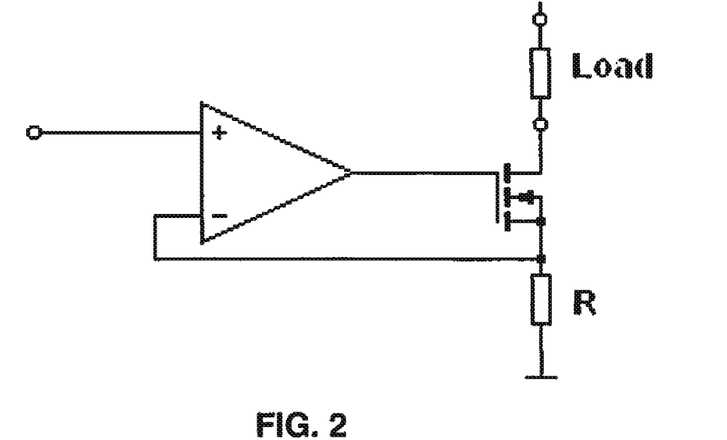
FIG. 2 shows diagrammatically a unipolar current source from the prior art.

FIG. 2 shows, in a simplified manner, such a unipolar current source in which "load" is again the load resistor, for example as defined above. The disadvantageous factor is here, among other things, that defined currents are difficult to implement due to the unipolarity.

As a solution to the problems mentioned, a circuit principle for constant current sources for stimulation in the medical field, primarily for supplying pacemakers with current, is shown in Offenlegungschrift US 2010/0324618. This contains an H bridge (for example identified by the reference symbol 330 in FIG. 5 there, or by the reference symbol 160 in FIG. 2 there).

Figure 3:
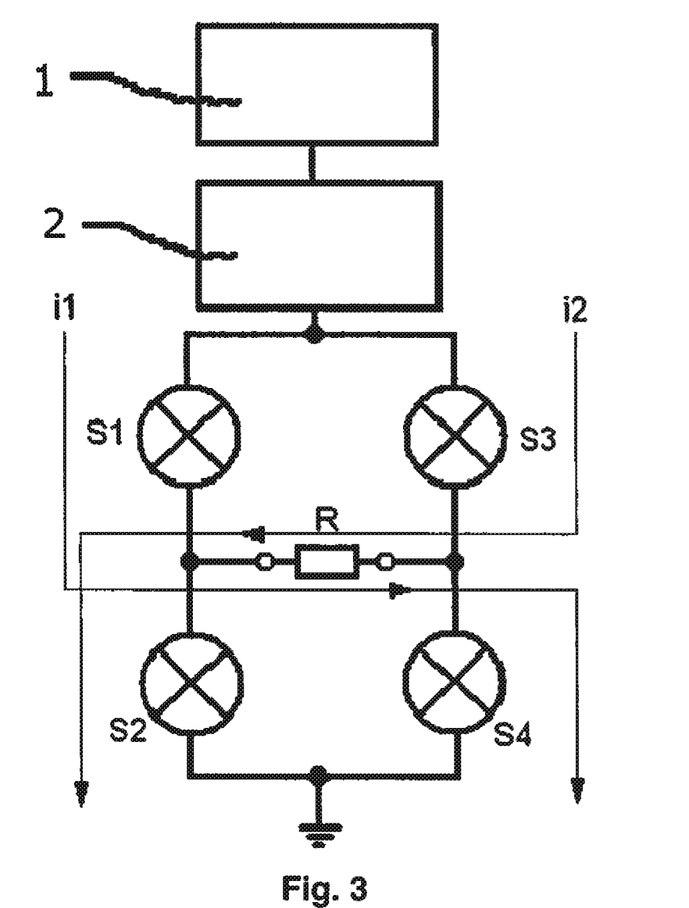
FIG. 3 shows a simplified diagrammatic representation of a circuit for constant current sources according to the teaching from the published patent application US 2010/0324618 (prior art).

FIG. 3 shows a simplified representation of the circuit shown for this current source.

In this Figure, 1 is a voltage source, 2 is an adjustable centralized constant current source (which could also be arranged at the lower end of the circuit after the combination of the legs with S2 and S4). When the switching elements S1 and S4 are closed, a (for example positive) current i1 (indicated by arrows in FIG. 3) can flow via the load resistor R (e.g. as defined above) interconnected in the bridge branch by applying the voltage while S2 and S3 are open. An alternative (for example negative, antiphase) current i2 (indicated by arrows in FIG. 3) can flow via the load resistor R by switching on S2 and S3, applying an opposite voltage. This H bridge thus allows the advantage of a biphase constant current source (e.g. for stimulation) when using an asymmetric supply voltage since the two connections (polarization) of the load can be simply exchanged by switching the switching elements.

Due to the principle involved, however, this circuit makes high demands on the timing precision of the switches and of the current source in the case of a change of direction of the current, especially when the positive and the negative direction of current are different. In the case of an inaccurate switch-over, a wrong current value may flow from time to time because, e.g., the new current value (current source 2, FIG. 3) is set, but still flows in the wrong direction through the load because the switch-over of the switches has not yet taken place. In addition, the circuits in US 2010/0324618, which is now U.S. Pat. No. 8,155,740 issued on Apr. 10, 2012, are designed rather for relatively low open-circuit voltages due to their orientation for stimulation of pacemakers which need rather low voltages.

SUMMARY

Against this background, the aim of the present invention is to provide a circuit arrangement, mentioned initially, in which the current intensities are adjustable and which permit a very low quiescent-current requirement and a wide open-circuit voltage range.

This aim is achieved in that, instead of one current source such as or analogous to the current source shown in FIG. 3, at least two conventional uniphase current sources with low quiescent current consumption (low quiescent power) are coupled by means of an H bridge (which can also have correspondingly more arms and switching elements in the case of more than two current sources) in such a manner that in each case one of these current sources handles one of the constant currents (especially one polarity) so that always only one of the current sources is active at one time via the load (load resistor). In other words, compared with the prior art shown in FIG. 3, two of the switching elements of an H bridge are extended by in each case one current source function and the centralized current source 2 at the top or at the bottom of the circuit arrangement in FIG. 3 is removed. In the case of a zero-current phase, one or more current sources can be deactivated in order to save current. For example, in a switch-over phase (e.g. repolarization at load resistor R), apart from the first current source already active, another one can be activated already shortly before the switch-over, after that the switches can be switched over and the first current source can then be deactivated. When conventional components are used, the switch-over phase can have a duration in the range of a few microseconds, for example in the range of about 10 to about 20 μsec, which helps to provide steep pulse edges. By activating and deactivating the current sources, the power demand can thus be minimized. As an alternative, all current sources can be activated permanently. It is possible to short-circuit the circuit without the current sources by correspondingly setting the switching elements. Thus, an optionally provided capacitive charge of a capacitance (e.g. a capacitor) connected—optionally—in series with the load resistor, e.g., on the bridge branch, which has been built up during the current flow (e.g. by charging the capacitor), can be removed. In the zero-current phase, the energy consumption is minimized. The presence of at least two current sources also enables very large voltage differences (for example from up to +500 to up to −500 V, e.g. within a range of up to +/−400 volts) to be built up with a very steep phase attack (that is to say very rapidly) without there being any switching problems or unwanted superimpositions.

The advantages of the arrangement according to the invention are thus, among other things, the provision of a large open-circuit voltage range (for example within a range of up to +/−400 to 500 V), a low power demand (scarcely any quiescent currents), short possible switch-over times between the different currents, steep possible rises (steep pulse edges, rapid adjustment of the constant current) of the voltages and possible currents during switch-over and simple and accurate controllability. As a result, it becomes possible to generate voltages which are sufficient for stimulating brain areas, such as those from the motor cortex, from the outside in patients, for example during operations in the cranial area (especially transcranial stimulation), and thus to check at the effector muscles whether the stimulus is still forwarded, for example in the case of operations on the brain or spinal cord or in areas in which corresponding motor neurons can be damaged.

In a first embodiment, therefore, the invention relates especially to an electronic circuit arrangement, as mentioned initially, which is characterized by the fact that it has (instead of one centralized current source) at least (and preferably only) two current sources (adjustable if desired), optionally having in each case at least one associated or integrated switching element, wherein especially one of them, a first current source, in each case provides for a first current (e.g. I1) via a first leg, which is connected to one end of the bridge branch, through the bridge branch and through a second leg, connected to the other end of the bridge branch opposite to the leg 3, when a first switching element in the first leg and an optional second switching element (advantageously for saving power and thus preferably present), which can be provided separately or preferably integrated in the first current source, in the second leg is correspondingly switched on, whilst the other one, a second current source, in each case provides for another current (e.g. I2) via a third leg, which is connected to the end of the bridge branch which is opposite to the end of the bridge branch to which the first leg is connected, through the bridge branch and through a fourth leg, connected to the other end of the bridge branch, when a third switching element in the third leg and an optional fourth switching element (advantageously for saving power and thus preferably present), which can be provided separately or preferably integrated in the second current source, in the fourth leg is correspondingly switched on, if in each case a load resistor R renders the bridge branch to have continuity. Advantageously, the current sources are here coupled as constant-current sources (provided for equally or not equally strong currents in comparison with one another) in such a manner that in each case only one of the current sources handles one polarity of the constant current through the load resistor R so that only one current source is active at any time via the load resistor R. For the zero-current phase, both current sources are not part of a closed circuit and the load circuit is advantageously designed to be short-circuitable. Advantageously, only one controllable voltage source can be provided in this context or each current source can have its own voltage supply.

In this arrangement, the first and third legs are above, the second and fourth legs are below the bridge branch in the circuit projected in an H shape.

The current sources are positioned preferably within the legs in each case.

In this context, a special embodiment of the invention relates to such an electronic circuit arrangement having two current sources which are connected via legs, connected to in each case opposite ends of the bridge branch, of an H bridge circuit (having four legs). The current sources are here advantageously combined with the second and fourth switching elements.

A further special embodiment of the invention relates to an electronic circuit arrangement according to one of the two immediately preceding paragraphs, wherein it also has electrodes (especially flat or cylindrical (for gripping) electrodes or needle electrodes (for puncturing)) at ends of the bridge branch, thus interrupted, of the bridge circuit which provide for an application or puncturing at a patient (as load resistor), a tissue or an organ or a body part of a patient.

A special embodiment of the invention also relates to an electronic circuit arrangement according to one of the three immediately preceding paragraphs which has (especially in the bridge branch) a capacitance, especially a capacitor.

In a further embodiment of the invention, the electronic circuit arrangement has, especially according to one of the four immediately preceding paragraphs, additionally at least one control device, especially for switching the switching elements on and off and/or for adjusting the current values provided by the current sources. In the case where the current sources have their own voltage sources, these, too, can also be designed to be controllable with regard to the voltages.

In further possible embodiments according to the invention, the electronic circuit arrangement mentioned in the preceding and following text contains, as current sources, combinations of operational amplifiers and switching elements, especially in the form of transistors or field-effect transistors such as MOS-FETs (e.g. power MOS-FETs).

A further embodiment of the invention relates to a method for, especially, intraoperative stimulation, in which a circuit arrangement according to the invention, defined as above or in the text which follows, is used for producing stimulation currents and a reaction is measured at an effector organ, e.g. a muscle twitch and/or a pressure or electromyographic signal, in order to be able to check whether a nerve connection or a brain area which is required for conducting the stimulus to the effector organ or forming the stimulus required for this is intact or wholly or partially damaged.

A further embodiment relates to a procedure for especially intraoperative determination of damage of a nerve connection or of a brain area in which the preceding method is used.

The invention also relates to using a circuit arrangement according to the invention, described in the preceding or following text, in which it is used for producing stimulation currents which act on a patient and a reaction is preferably measured at an effector organ, e.g. a muscle twitch and/or a pressure or electromyographic signal, in order to be able to check whether a nerve connection or a brain area which is required for conducting the stimulus to the effector organ or forming the stimulus required for this is intact or wholly or partially damaged.

The circuit arrangements according to the invention, configured for performing the said methods and uses, for generating at least two different constant currents also form an embodiment of the invention.

Further special embodiments of the invention are found in the claims and especially the dependent claims, and in the examples. The claims are included here by reference.

If it is not immediately apparent to the expert, the expressions used in the preceding and following text preferably have the following meanings unless otherwise specified, in which context one or more or all of the general expressions can be replaced independently of one another in each case by the subsequent definitions which results in special embodiments of the invention.

Adjustable means that the voltages and thus the possible currents of the current sources can be controllable. However, constant current sources can also be used which can only be switched on and off.

Polyphase means that voltages of different intensity, for example and especially opposite polarity, can be applied to the load resistor. In this context, biphase means especially that two voltages of opposite polarity (which can lead to currents in the negative or positive direction), preferably voltages of equal magnitude, can be applied to the load resistor. Uniphase means especially identical current direction (polarity).

The currents through the bridge branch are primarily direct currents within a certain period (e.g. the period between the switch-over).

As a "load resistor", one or more body parts (e.g. arm, leg or especially head), a tissue or an organ of patients, as mentioned, can bridge the otherwise open bridge branch with electrodes during an operation on a patient.

"Patient" means an animal to be examined (e.g. mammal) or especially a person to be examined who can be healthy or sick.

Generation of at least two different stimulation currents (polyphase stimulation) in medicine means especially that two or more, especially two, different, especially antiphase currents (currents of opposite direction) are used for the stimulation. The stimulation preferably occurs during an operation (intraoperatively) which necessitates that the electronic circuit arrangements according to the invention are correspondingly configured, especially provide for voltages within a range of up to +/−500 volts, e.g. of up to +/−400 volts, which also permit stimulation from the outside, have electrodes which can be attached reversibly (for example by application or puncturing) at patients (that is to say for example contain no elements for permanent fixing in or at patients as required in the case of pacemakers) and which provide for clearly defined currents. Thus, for example, the integrity of nerves can be checked during an operation by the presence or the restriction or the lack of reactions of the musculature in the case of integrity or injury to nerve tracks or brain areas and, if necessary, measures can be taken in order to avoid threatening damage or counter unintentionally intra-operatively caused damage already during the operation.

A switching element which is allocated to a current source or integrated in it can be a separate switching element such as an electronic or mechanical switch in the first case, or, in the second case, it can be an integrated component of the current source and/or also form the latter, for example as a current source in the case of current/voltage converters, an input voltage of zero (0) volts meaning that no current is flowing (see also the explanations relating to FIG. 8 below) and thus the switching function is implemented directly in the current source.

"Current value" means the current intensity, open-circuit voltage means the voltage without load (open load, i.e. infinitely high load resistance R).

DETAILED DESCRIPTION OF THE PREFERRED EMBODIMENTS

The description of the figures and the figures themselves represent special embodiments of the invention.

The subsequent example and the figures are used for illustrating the invention without restricting its range. The individual exemplary features can also be used instead of general defined features mentioned in the preceding and following text, individually, in several or all embodiments, mentioned outside the example, of the invention instead of general features used there.

The position of the voltage sources 1 in the subsequent figures should only be considered as an exemplary arrangement—instead, the voltage source can also be implemented at the bottom (below the node of legs 4 and 6 or thereon) as component of IS1 or IS2 or as component of S1 and S2.

Figure 4:
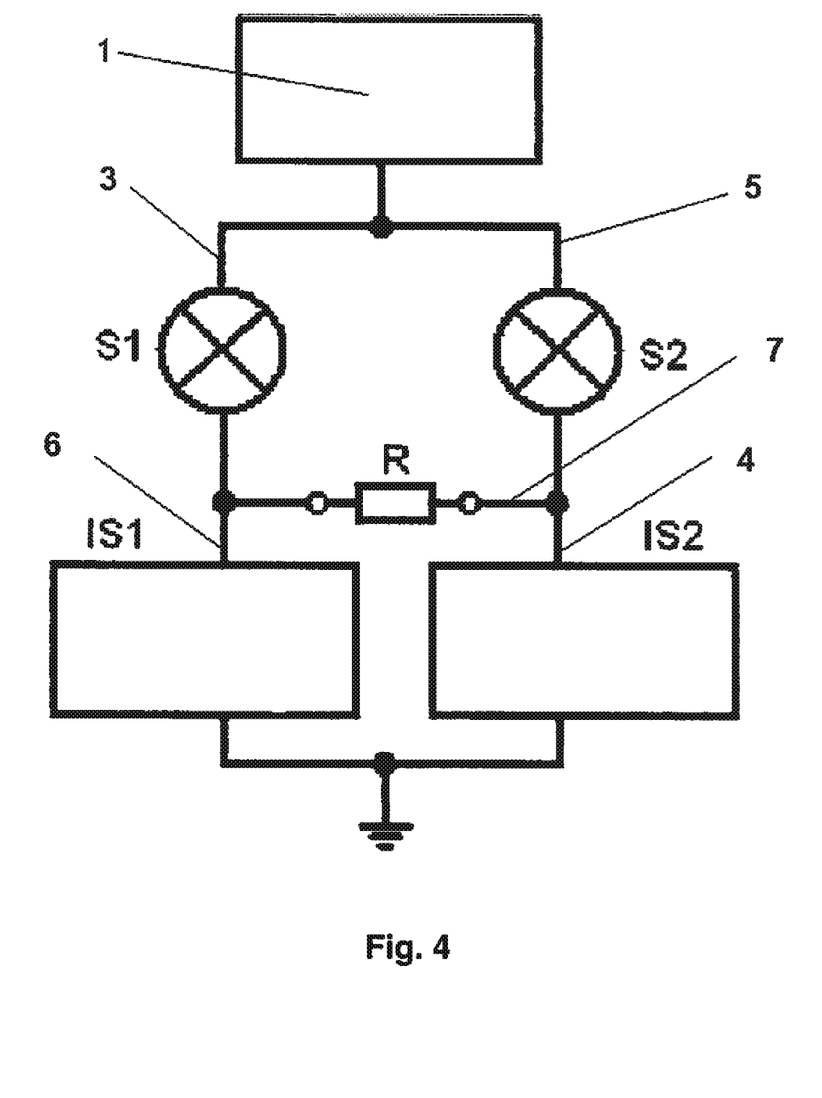
FIG. 4 shows diagrammatically a simplified representation of a possible embodiment of an electronic circuit arrangement according to the invention in the currentless state.

FIG. 4 shows an example of a circuit arrangement according to the invention in which a voltage source 1 advantageously designed to be controllable with regard to the voltage which can be picked up (which voltage source, for example, steps up a voltage (approx. 4.75 to 5.25 V, as a rule) resulting from a suitable interface (i.e. providing for an adequate basic voltage) such as a USB terminal e.g. of a computer or of a power supply which provides for particularly simple handling) is connected via a branch to the first leg 3 and the third leg 5 of an H bridge. In the leg 3, a first switching element S1 is located, in the leg 5 a third switching element S2 is located. The switching elements can be mechanical or especially electronic switches. The legs 3 and 5 are connected at their lower ends to a bridge branch 7, here shown with inserted load resistor R (e.g. patient, e.g. head of a patient). A second leg 4 and a fourth leg 6, respectively, are also connected to the lower end of the legs 3 and 5, respectively, and the ends of the bridge branch 7, which legs 4 and 6 are connected at their opposite ends to a counter pole with respect to the voltage source 1, symbolized by way of example by the grounding/ground shown.

The fourth leg 6—shown here as a combination but also constructible separately—contains a combination IS1 of a second switching element and a first current source, the second leg 4—shown here as a combination but also constructible separately—contains a combination IS2 of a fourth switching element and a second current source. IS1 and IS2 do not need to be mandatorily switchable, in the sense of simplifying the current switch-over, the switching elements can be lacking or the current sources themselves have a switching function at the same time (one of the variants in which the switching element is integrated into the current sources IS1 and/or IS2). On the other hand, they are advantageously switchable (especially for power saving) or active as switching elements, for example, as described further below according to FIG. 8 (another variant in which the switching element is integrated into the current sources IS1 and/or IS2).

The load resistor (for example a body part of a patient such as his head) is connected into the bridge branch 7 between two electrodes, symbolized by small circles, which, for example, can be designed as flat electrodes or as piercing electrodes. In addition, the bridge branch 7 can contain a capacitance—not shown in FIG. 4-*such* as a capacitor.

The current sources can be configured, for example by using suitable resistors and/or by opposite polarization compared with the respective other current source, for delivering different current intensities or preferably for delivering identical current intensities and/or (especially and) currents by identical polarization.

Instead of one voltage source (1) as shown, the current sources can also have in each case a separate voltage source.

The current sources can be designed advantageously as voltage/current converters. No additional switching element is then needed—at an input voltage of zero volts, no current flows then, that is to say, no separate "switch" is needed here. The current sources can be designed, for example, as operational amplifiers (possibly also in accordance with the Howland principle which, however, is not required here).

The switching elements in the form of electronic switches can contain field-effect transistors such as, especially MOS-FETs or other suitable (e.g. mechanical or relay) switches.

Other possible components of a circuit arrangement according to the invention, which are familiar to the expert, such as control devices (which can be connected via lines or radio or light signals) for the switching elements and other lines or conventional components, are not shown.

The operation of a circuit arrangement according to the invention is shown by way of example by way of FIGS. 5 to 7 and 9 (identical reference symbols having the same meanings as in FIG. 4).

Figure 5:
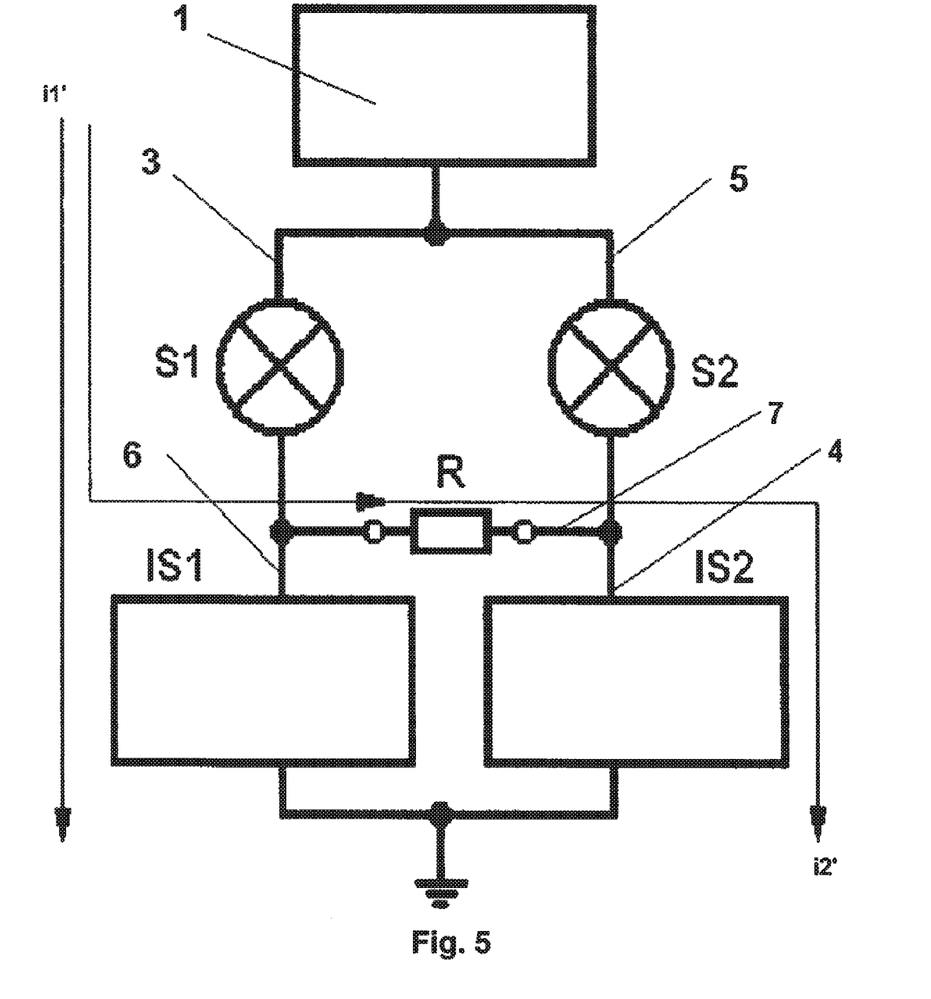
FIG. 5 shows diagrammatically a simplified representation of a possible embodiment of a circuit according to the invention with current flowing through the switching element S1 and the current source with switching element IS2.

If, as in FIG. 5, the first switching element S1 is closed and the third switching element S2 is open, a current i2' flows through the load resistor R, driven by the current source IS2. The current i1' of the current source IS2 can also flow through S1, and therefore not through the load R.

Figure 6:
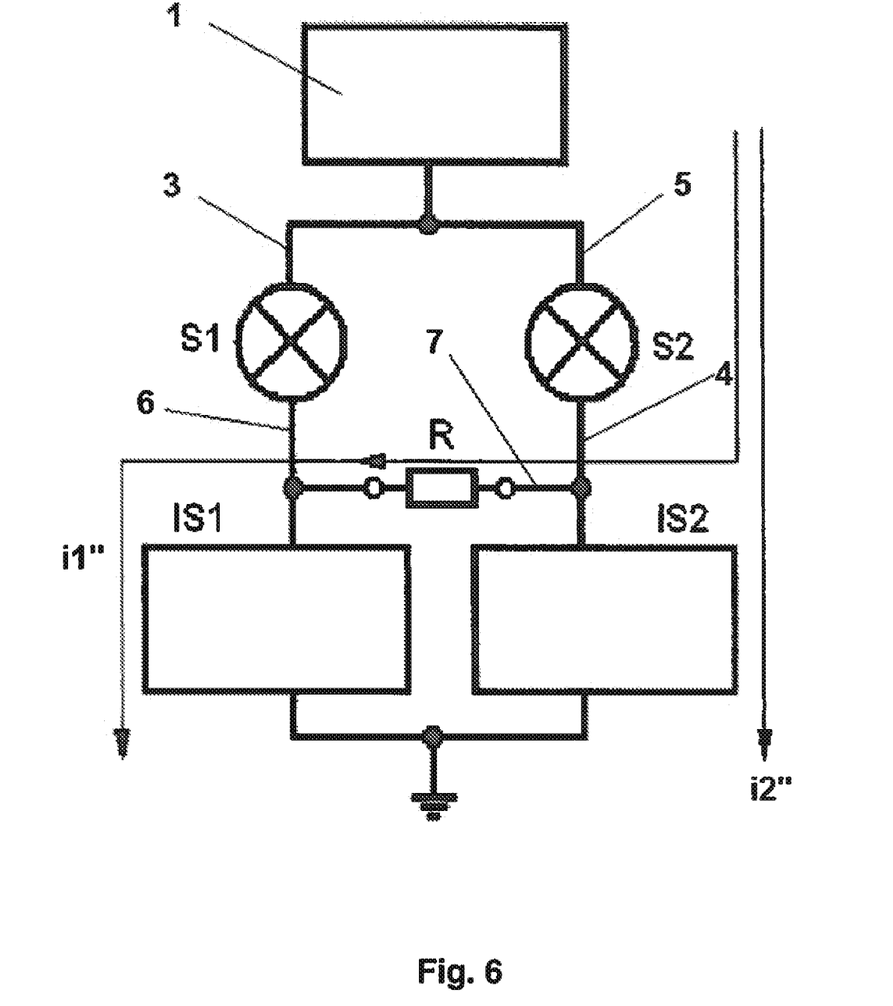
FIG. 6 shows the reverse situation with respect to that shown in FIG. 5, in the form of a diagrammatic simplified representation of a possible embodiment of a circuit arrangement according to the invention with current flowing through the switching element S2 and the current source with switching element IS1.

If, as in FIG. 6, the first switching element S1 is open and the third switching element S2 is closed, a current i1'' flows through the load resistor R, driven by the current source IS1. The current i2' of the current source IS1 can also flow through S2 and therefore not through the load R.

Figure 9:
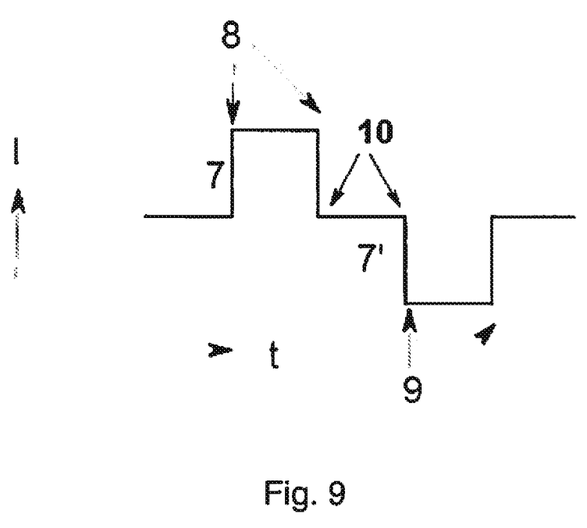
FIG. 9 shows, in a simplified manner, an example of a current pulse curve.

If, in a possible advantageous embodiment of the invention, for example, IS1 and IS2 are of the same polarity and they generate equally strong currents, an equally strong, but opposite current (antiphase current or current of opposite polarity) flows in each case from IS1 and IS2 through the bridge branch 7 comprising the load resistor R. This is illustrated by FIG. 9:

When the situation according to FIG. 5 is switched on, a constant current 8 is produced via a steep pulse edge 7, when both switches S1 and S2 are opened, a quiescent phase 10 without current can be interposed optionally or it can be lacking (it is then possible to switch very rapidly from the first one to the opposite polarity), whereas, when the situation according to FIG. 6 is switched on, a constant current 9 flows in the opposite direction to 8 via a steep pulse edge 7' in both cases.

Nevertheless, circuit arrangements according to the invention are also conceivable in which the currents from IS1 and IS2 are of different intensity or the current sources in IS1 and IS2 do not have the same polarity so that, on switch-over between the situations in FIG. 5 and FIG. 6, two different, not mandatorily opposite currents can result. This provides for, for example, special stimulation patterns or other applications of the circuit arrangements according to the invention.

Figure 7:
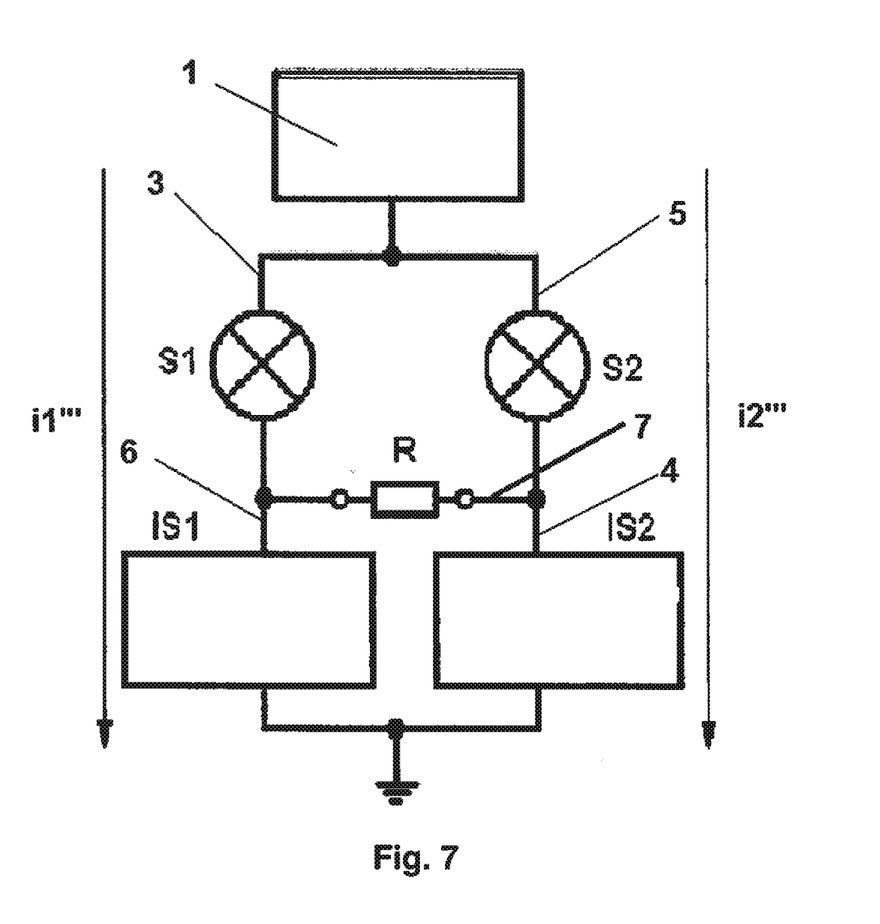
FIG. 7 shows diagrammatically a simplified representation of a possible embodiment of a circuit arranged according to the invention, in which, after the closing of both switching elements in the current sources with switching elements, no current flows over the load resistor R whilst the switching elements S1 and S2 can be open.

FIG. 7 shows a situation in which both switching elements S1 and S2 are closed. In this case, no current flows through the load R. In addition, the load R is short-circuited via the switches. This provides the opportunity to reduce a charge stored, for example, in an optional capacitance such as a capacitor in the bridge branch 7 again or reduce a charge on the load R again.

In FIGS. 5, 6 and 7 control devices for switching the switching elements S1 and S2 and the switchable current sources IS1 and IS2 on and off are not shown, but these are comprised in preferred embodiments of circuit arrangements according to the invention. Corresponding control devices can be available, for example, as switching boxes or as computer-controlled units. The situation in which both currents i1''' and i2''' are active at the same time relates preferably only to the interval of the change in current value or especially direction of current (switch-over phase) through the load resistor R. In order to achieve power savings, the current source not effective via the power resistor R is preferably switched off after the switch-over phase (current value set to zero).

If fixed current values are provided for both directions, a simple opportunity of deactivating the current source is sufficient in the case of the embodiments according to the invention. For medical application, however, the use of different (controllable) current values is prevalent and is to be preferred. For this reason current sources according to the principle of the current/voltage converter are provided here, as a rule. In this arrangement, the current value is determined by an equivalent input voltage (which can be supplied, e.g., by means of a control device).

FIG. 1 and FIG. 2 represent such current/voltage converters. At the positive (+) input of the operational amplifier (OPA), a control voltage is applied, the amplitude of which, due to the circuit, leads to a constant current through the load. If the control voltage is zero (=volt), the load current is also zero (zero ampere), taking into consideration correct dimensioning. To this extent, the circuits quoted can also fulfill the "off" function of a switch. For FIG. 8, points "b" and "d" are the inputs of the respective control voltage which can be provided, for example, by means of a D/A converter.

It is possible to provide other units, for example for controlling the voltage in the voltage source, for controlling the current intensity and direction in the current sources such as IS1 and IS2, for measuring the currents and voltages, for feedback control of the current intensity, for measuring reactions of the patient (for example pressure build-up in muscles or electromyograms) and the like. These can be connected via lines or radio or (for example IR) light.

Figure 8:
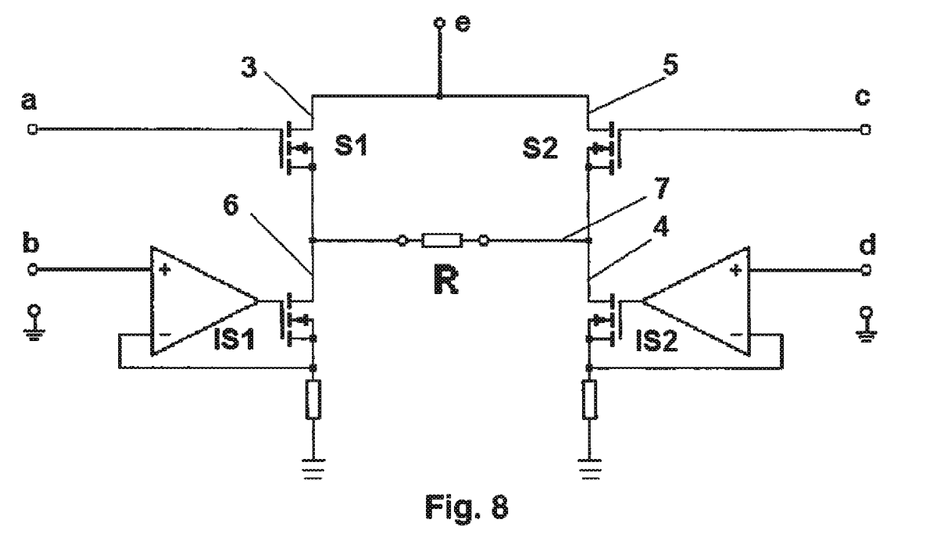
FIG. 8 shows as a simplified circuit diagram a possible embodiment of a switching arrangement according to the invention.

FIG. 8 shows a more special variant of a circuit arrangement according to the invention for the exemplary illustration of possible circuits. The operational amplifiers (OPA) are shown without supply terminals. The reference symbols 3 to 7, S1, S2, IS1 and IS2 and R correspond to the meanings mentioned above for FIGS. 5 to 7, whilst a, b, c and d are symbolic for terminals, for example for a control device.

Exemplary actual embodiments of the circuit arrangement elements shown in FIG. 8 can be characterized as follows:

With a voltage of from 0 to 2.5 V at IS1 for driving IS1 via (b), a current intensity of from 0 to 250 mA can be set. The same applies to IS2 via (d).

The voltage source (starting from pole e) can be provided, for example, for a controllable voltage within a range from 0 to 400 volts.

The MOS-FETs S1 and S2 can be those of the conventional type such as, for example, of type IRFU3910 (International Rectifier, El Segundo, Calif., USA).

The MOS-FETs as a component of IS1 and IS2 can be, for example, those of type STD3NK60 (ST Microelectronics, Geneva, Switzerland).

The operational amplifiers as a component of IS1 and IS2 can be those of type LTC 2050 (Linear Technology Corp., California, USA).

The resistors leading to ground (the bottom two in FIG. 8) are determined by the dimensioning of the voltage/current converter and can be 10Ω, e.g., for the range mentioned above.

The switching voltage for the switches S1 and S2 depends on the magnitude of the open-circuit voltage at point (e) and is, e.g., 390 V for "on" and 400 V for "off", e.g. with an open-circuit voltage of 400 V.

The invention claimed is:

1. An electronic circuit arrangement for generating at least two different constant currents at a load resistor R, comprising:
   a bridge circuit having at least first, second, third and fourth legs (3, 4, 5, 6), and switching elements S1 and S2 and a bridge branch (7) between the legs, in which the load resistor R is inserted, and at least first and second current current sources (IS1, IS2) connected to the legs of the bridge circuit in such a manner that the current sources provide for a current via one of the legs through the bridge branch (7) through one of the legs, connected to an other end of the bridge branch (7) in the case of a corresponding switch position,
   the first current source (IS2) in each case provides for a first current I1 (i2') via the first leg ((3) or (4)), which is connected to one end of the bridge branch (7), through the bridge branch (7) and through the second leg ((4) or (3)), connected to the other end of the bridge branch (7) opposite to the first leg ((3) or (4)), when a first one of the switching elements (S1) in the first leg ((3) or (4)) and an optional second switching element, which can be provided separately or integrated in the first current source (IS2), in the second leg ((4) or (3)) is correspondingly switched on,
   the second current source (IS1) case provides for another current I2 (i1') via the third leg ((5) or (6)), which is connected to the end of the bridge branch (7) which is opposite to the end of the bridge branch (7) to which the first leg ((3) or (4)) is connected, through the bridge branch (7) and through the fourth leg ((6) or (5)), connected to the other end of the bridge branch (7), when a third one of the switching elements (S2) in the third leg ((5) or (6)) and an optional fourth switching element, which is provided separately or integrated in the second current source (IS1) in the fourth leg ((6) or (5)) is correspondingly switched on,
   when in each case the load resistor R renders the bridge branch (7) to have continuity.

2. The electronic circuit arrangement as claimed in claim 1, wherein
   the first current source (IS2) in each case provides for a first current I1 (i2') via the first leg (3), which is connected to one end of the bridge branch (7), through the bridge branch (7) and through the second leg (4), connected to the end of the bridge branch (7) opposite to the first leg (3), when the first switching element (S1) in the first leg (3) and the optional second switching element, which can be provided separately or integrated in the first current source (IS2), in the second leg (4) is correspondingly switched on,
   whilst the second current source (IS1) in each case provides for another current I2 via the third leg (5), which is connected to the end of the bridge branch (7) which is opposite the end of the bridge branch (7) to which the first leg (3) is connected, through the bridge branch (7) and through the fourth leg (6), connected to the other end of the bridge branch (7), when the third switching element (S2) in the third leg (5) and the optional fourth switching element, which can be provided separately or integrated in the second current source (IS1), in the fourth leg (6) is correspondingly switched on,
   when the load resistor R in each case renders the bridge branch (7) to have continuity.

3. The electronic circuit arrangement as claimed in claim 1, wherein there are exactly two of the current sources (IS1, IS2) which are connected via the legs, connected to in each case opposite ends of the bridge branch (7), of an H bridge circuit having four of the legs.

4. The electronic circuit arrangement as claimed in claim 3, wherein the current sources (IS1) and (IS2), respectively, contain the second and the fourth switching element, respectively, and the first switching element (S1) is provided in the first leg (3) and the second switching element (S2) is provided in the third leg (5) and the first current source (IS1) is provided in the second leg (4) and the second current source (IS2) is provided in the fourth leg (6).

5. The electronic circuit arrangement as claimed in claim 1, wherein there are two electrodes at the ends of the bridge branch (7), that is thus interrupted, of the bridge circuit which provide for an application or puncturing at a patient, a tissue or an organ or a body part of a patient which signify the load resistor R.

6. The electronic circuit arrangement as claimed in claim 5, wherein the electrodes are flat, cylindrical or needle electrodes.

7. The electronic circuit arrangement as claimed in claim 1, further comprising a capacitance also located in the bridge branch (7).

8. The electronic circuit arrangement as claimed in claim 1, further comprising a control device.

9. The electronic circuit arrangement as claimed in claim 1, wherein the current sources (IS1, IS2) are provided as current/voltage converters, including combinations of operational amplifiers and the second and fourth switching elements (4, 6) in the form of field-effect transistors.

10. The electronic circuit arrangement as claimed in claim 1, wherein the current sources (IS1, IS2) have a same polarity and provide for currents which are equally strong but flow oppositely through the bridge branch (7).

11. The electronic circuit arrangement as claimed in claim 1, wherein the current sources (IS1, IS2) provide for identical or different polarity and differently strong currents flowing through the bridge branch (7).

12. The electronic circuit arrangement as claimed in claim 1, wherein there are biphase currents, a polarity of which alternates directly or via a quiescent current phase.

13. The electronic circuit arrangement as claimed in claim 1, wherein the current sources (IS1, IS2) are constant current sources and are connected or coupled via the associated switching elements or switching elements integrated therein and the first and the third switching element (S1, S2) in such a manner that in each case only one of the current sources handles a polarity of the constant current through the load resistor R so that only one current source is active at any time and the first and third leg (3, 5) can be short-circuited by closing the switching elements (S1, S2) while the switching elements in the current sources (IS1, IS2) are open so that a charge can flow off at a capacitance inserted in the bridge branch (7).

14. A method for intraoperative stimulation, in which an electronic circuit arrangement defined according to claim 1 is used for producing stimulation currents and a reaction is measured at an effector organ in order to be able to check whether a nerve connection or a brain area which is required for conducting a stimulus to the effector organ or forming the stimulus required for this is intact or wholly or partially damaged.

\* \* \* \* \*